United States Patent [19]

Prodl

[11] Patent Number: 4,606,232
[45] Date of Patent: Aug. 19, 1986

[54] DEVICE FOR SEPARATING AIRBORNE PARTICLES IN DEPENDENCE ON GRAIN SIZE

[76] Inventor: Vittorio Prodl, Via Martinelli, 7, 40137 Bologna, Italy

[21] Appl. No.: 723,820

[22] Filed: Apr. 16, 1985

[30] Foreign Application Priority Data

Apr. 19, 1984 [IT] Italy .................................. 3434 A/84

[51] Int. Cl.$^4$ ................................................ G01N 1/00
[52] U.S. Cl. ................................................. 73/863.23
[58] Field of Search ............ 73/863.21, 863.22, 863.23, 73/432 PS; 209/37, 141, 143

[56] References Cited

U.S. PATENT DOCUMENTS 3,854,321 12/1974 Dahneke ..................... 73/432 PS X
4,213,852 7/1980 Etkin ............................ 73/432 PS X Primary Examiner—Jerry W. Myracle
Attorney, Agent, or Firm—Omri M. Behr

[57] ABSTRACT

A device is described for separating airborne particles into classes depending on grain size. The principle characteristic of the present invention lies in the fact that it comprises:

a hollow base body, in which, in use, a depression is created;

an upper body in which is formed a channel to which there is conveyed, in use, the particle-bearing air and which has a lower extremity with a circular outline;

a mesh positioned between the said base body and the said upper body and on which is positioned a filter defining, with the lower face of the said upper body, a cavity; and a nozzle housed in the said channel and operable to eject filtered air in proximity to the said lower end of this latter in such a way that the particles flowing through the said lower end are separated into various bands according to their aerodynamic diameter and are deposited on the said filter.

9

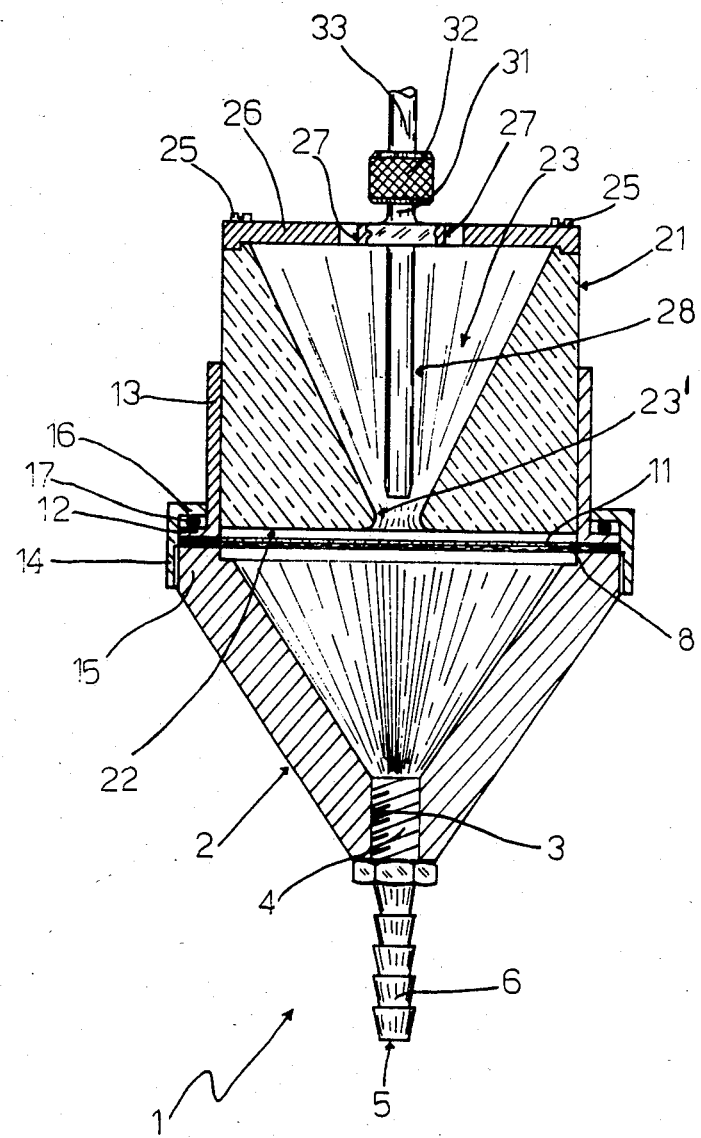

DEVICE FOR SEPARATING AIRBORNE PARTICLES IN DEPENDENCE ON GRAIN SIZE

BACKGROUND OF THE INVENTION

The present invention relates to a device for separating airborne particles into classes determined by grain size, adapted for use as a personal sampler able to be carried by the user in order to determine the risk to the user from inhalations.

As is known, in currently used devices the grain size information is provided by a pre-selector, which simulates the extrathoracic and tracheo-bronchial passages, and by a filter. In the pre-selector, which is normally constituted by a cyclone, the particles of larger diameter are deposited, and in the filter the particles of smaller diameter are deposited.

SUMMARY OF THE INVENTION

The object of the present invention is that of providing a device for separating airborne particles into grain size classes, in which the technique of inertial separation is applied in such a way as to separate the fraction of the particles having a greater diameter into two grain size classes in order to obtain a greater amount of information relating to this latter.

Further objects and advantages will become apparent in the following description.

According to the present invention there is provided a device for separating airborne particles into grain size classes, characterised by the fact that it comprises:

a hollow base body in which, in use, there is created a depression by means of an external member;

an upper body along the longitudinal axis of which is formed a through channel into which is conveyed, in use, the particle-bearing air, and which has a lower end of circular outline;

a mesh positioned between the said base body and the said upper body and operable to support a filter defining, with the lower face of the said upper body, a cavity which is in good communication through the said lower end with the said through channel; and a nozzle in the said channel operable to eject, in proximity to the said lower end of this latter, filtered air in such a way that in the fluid formed by the particle-bearing air and the filtered air after having traversed the said lower end, the particles are separated into various bands according to their aerodynamic diameter and are deposited on the upper surface of the said filter starting from the particles of greater diameter.

DETAILED DESCRIPTION OF THE INVENTION

For a better understanding of the present invention there will now be described a preferred embodiment purely by way of non limitative example, with reference to the attached drawing in which there is illustrated a section of the device of the invention, which has been generally indicated with the reference numeral 1. This device comprises a base body 2 formed substantially as a funnel with upwardly facing concavity. In the lower part of the body 2 there is formed a threaded hole 3 engaged by an upper threaded portion 4 of a pipe union 5 a lower portion 6 of which, outside the hole 3, supports in use the end of a duct (not illustrated) which can put a pump into communication with the interior of the body 2 in order to create therein a depression. On the upper edge of the body 2 rests a mesh 8 of circular outline and on this is deposited a filter 11, also of circular outline. The assembly comprising the mesh 8 and the filter 11 is pressed between the upper edge of the body 2 and an annular flange 12 extending outwardly from a lower end of a sleeve 13 coaxial with but positioned above the body 2. The device 1 further includes a ring 14 which is threaded internally and which can be screwed onto a threaded portion 15 of the body 2, formed on the outer wall thereof. From the upper end of the ring 14 there extends, inwardly, an annular flange 16, and between the lower surface of this latter and the upper surface of the flange 12 there is disposed a sealing ring 17. In use, by screwing the ring 14 onto the portion 15, the flange 16 presses the flange 12 downwardly, which compresses the assembly defined by the filter 11 and the mesh 8 onto the upper edge of the body 2. In order to hold the mesh in tension the perimetral edge of this extends outwardly between the flange 12 and the upper edge of the body 2 in such a way that it is drawn downwardly by the inner surface of the ring 14 during its screwing onto the portion 15.

As illustrated in the attached drawing, within the sleeve 13 there is lodged the lower part of cylindrical body 21 coaxial with the body 2 the lower surface of which faces the filter 11 and is disposed at a predetermined distance therefrom in such a way as to define a cylindrical cavity 22. Along the longitudinal axis of the body 21 there is formed a through channel 23 which opens out at its lower end into the cavity 22 and which has a frusto-conical configuration with the region of greater diameter located in the uppermost part; the channel 23 therefore represents a nozzle which injects an aerosol into the cavity 22. For this purpose the channel 23 has a lower end, hereinafter termed the outlet end and indicated with 23', which has no sharp corners since these have been suitably rounded.

On the upper face of the body 21 there is fixed, by screws 25, a plate 26 of circular geometry in which there is formed a plurality of through holes 27 which can put the surrounding air in communication with the channel 23. Within this latter, and coaxially thereto, there is disposed a nozzle 28 which can inject filtered air in close proximity to the outlet 23'; the nozzle 28 is fixed to the plate 26, for example by welding and has an upper end 31 projecting out from the plate 26 and connected, by means of a connector element 32, with the end of a duct 33 which can put the interior of the nozzle 28 into communication with a source of filtered air.

The operation of the device 1 is as follows.

In detail, the said pump creates a depression within the body 2 which draws into the channel 23, via the holes 27, the aerosol generated by the air present in the surrounding environment and particles of dust which are in suspension therein. The pump also draws filtered air from the said source via the nozzle 28 and the fluid, formed from the aerosol and the filtered air, is drawn into the cavity 22 via the outlet 23'. The technique of inertial separation consists in the fact that the particles flowing past a sharp curvature, (outlet 23') by intertia tend to maintain their velocity in direction and sense, but are drawn by the flow of fluid; the particles therefore are displaced from the original streamline (which flows out downstream of the curvature) by a distance which is a function only of the aerodynamic diameter. Consequently the particles are separated according to diameter into various bands of fluid and all the particles of the same grain size will be present within their own streamline; after having traversed the curvature the particles begin to deposit onto annular portions of the filter 11 starting from the particles of greatest diameter. The fluid, cleaned of the particles, will subsequently enter into the interior of the body 2 towards the pump. Subsequently it is possible to extract the filter 11 and perform on the deposit all the chemical and physico chemical analyses which are considered necessary for the determination of the toxicity of the particles in suspension in the air and therefore in the inhalations of the user.

With the device of the invention there is attained on the filter 11 a continuous deposit of particles and, more precisely, a deposit of particles of greater diameter along the central annular portions and gradually of smaller diameter towards the peripheral annular portions of the filter 11. In order better to analyse the deposit it is possible to calibrate the device 1 in such a way as to separate the filter 11 into several parts, for example into three parts, in each of which there takes place the deposit of particles with a diameter lying within a predetermined interval; for example it is possible to separate the filter 11 into a first part which is that closest to the outlet 23' in which there occurs the deposit of particles with a diameter greater than 10 μm., second, central part, in which takes place the deposition of particles of the diameter lying between 2.5 or 3.5 μm. and 10 μm., and a third part which is the periphery in which there takes place the deposition of particles with a diameter less than 2.5 or 3.5 μm. It is apparent that if in the filter 11 there are provided reference indictions for delimiting the three parts, it is possible to cut these along the zones of separation between the various parts and therefor analyse individually the parts which are of greatest interest or all three parts to determine the characteristics of the three grain size fractions into which the particles have been separated. Normally the most interesting part for determining the toxicity of the air which the user breathes is the second, that is to say that having particles lying between 2.5 or 3.5 μm and 10 μm. The minimum threshold of such part can be 2.5 or 3.5 μm. according to the sensitivity of the user; the more sensitive the user is the lower the value of the threshold has to be.

It will be evident that the advantages which are obtained with the device 1 are those of having provided a portable instrument in which it has been possible to apply the technique of intertial separation, and of being able to proceed with ease in analysing the deposit subdivided into three grain size classes. It is to be noted that the inertial separation is assisted by the particular cylindrical geometry of the devce 1 in that with such geometry, it has been found experimentally, an elongation of the zones of separation between the particles of different diameters has been noted and therefore a better and clearer separation of the grain size classes of these. Further, the device is of simple construction and requires no particular maintenance operations, and is of low production costs.

Finally, it is clear that the device described and illustrated here can be modified and varied without by this departing from the protective scope of the present invention.

I claim:

1. A device for separating airborne particles into grain size classes, characterised by the fact that it comprises:

a hollow base body (2) in which, in use, there is created a depression by means of an external member;

an upper body (21) along the longitudinal axis of which is formed a through channel (23) in which, in use, particle-bearing air is conveyed, and which has a lower end (23') of circular outline;

a mesh (8) positioned between the said base body (2) and the said upper body (21) and operable to support a filter (11) defining with the lower face of the said upper body (21) a cavity (22) which is in communication, through the said lower end (23') with the said through passage (23);

a nozzle (28) within the said channel (23), operating to eject close to the lower end (23) of this latter, filtered air in such a way that the particles in the fluid comprising the particle-bearing air and the filtered air after having traversed the said lower end (23') are separated according to their aerodynamic diameter and become deposited on the upper surface of the said filter starting from particles of greater diameter.

2. A device according to claim 1, characterized by the fact that the said nozzle (28) is coaxial with the said channel (23).

3. A device according to claim 2, characterized by the fact that the said channel (23) has a cover plate (26) fixed on the upper face of the said upper body (21); therebeing formed on the said plate (26) at least a first hole (27) which can put the said channel (23) into communication with the environment surrounding the source of particle-bearing air.

4. A device according to claim 3, characterized by the fact that the said plate (26) supports the said nozzle (28) which is connected by means of a duct (33) with a source of filtered air.

5. A device according to claim 1, characterized by the fact that the said upper body (21) is of cylindrical configuration and the said base body (2) is formed as a funnel; the said base body (2) having a second threaded hole (3) engaged by an upper portion (4) of a pipe union (5) which can put the said member into communication with the interior of the said base body (2).

6. A device according to claim 5, characterized by the fact that the said mesh (8) and the said filter (11) are of circular geometry.

7. A device according to claim 6, characterized by the fact that the lower part of the said upper body (21) is lodged within the interior of a sleeve (13) and is supported by this latter; a first annular flange (12) extends outwardly from a lower end of the said sleeve (13) to press the peripheral edge of the assembly comprising the said mesh (8) and the said filter (11) onto the edge of the upper end of the said base body (2).

8. A device according to claim 7, characterized by the fact that the upper end of the said base body (2) has an externally threaded lateral portion (15) on which is screwed a ring (14) from the upper end of which extends, inwardly, a second annular flange (16) to press the said first flange (12) onto the upper end of the said base body (2).

9. A device according to claim 8, characterized by the fact that a sealing ring (17) is disposed between the said first flange (12) and the said second flange (16).

* * * * *